(12) United States Patent
Kirby et al.

(10) Patent No.: US 7,384,524 B2
(45) Date of Patent: Jun. 10, 2008

(54) DETECTION OF CARBON MONOXIDE IN HYDROGEN-BASED GAS STREAMS

(75) Inventors: Kevin Kirby, Calabasas Hills, CA (US); Keith C. Fuller, Los Angeles, CA (US)

(73) Assignee: HRL Laboratories, LLC, Malibu, CA (US)

( * ) Notice: Subject to any disclaimer, the term of this patent is extended or adjusted under 35 U.S.C. 154(b) by 518 days.

(21) Appl. No.: 10/386,901

(22) Filed: Feb. 27, 2003

(65) Prior Publication Data

US 2003/0234178 A1    Dec. 25, 2003

Related U.S. Application Data

(60) Provisional application No. 60/361,634, filed on Feb. 28, 2002.

(51) Int. Cl.
*G01N 27/407*    (2006.01)

(52) U.S. Cl. .................... 204/424; 205/784; 429/22

(58) Field of Classification Search ............... 204/421, 204/424, 431; 205/784; 429/12, 22, 30, 429/40
See application file for complete search history.

(56) References Cited

U.S. PATENT DOCUMENTS 3,678,375 A * 7/1972 McFarland et al. ......... 324/425
5,272,017 A * 12/1993 Swathirajan et al. ........... 429/33
5,302,274 A    4/1994 Tomantschger et al.
5,683,828 A * 11/1997 Spear et al. .................. 429/13
5,945,229 A *  8/1999 Meltser ........................ 429/13
6,001,499 A * 12/1999 Grot et al. .................... 429/22
6,117,577 A *  9/2000 Wilson ........................ 429/17
6,306,285 B1 * 10/2001 Narayanan et al. ......... 205/787
6,527,943 B1 *  3/2003 Zhang et al. ............... 205/787

FOREIGN PATENT DOCUMENTS

EP             0710996 A      5/1996
EP             1156326 A     11/2001
WO          WO 0211225 A      2/2002

* cited by examiner

*Primary Examiner*—Kaj K. Olsen
(74) *Attorney, Agent, or Firm*—Cary Tope McKay (57) ABSTRACT

The present invention relates to a sensor for and a method of detecting carbon monoxide in gas streams containing hydrogen. The sensor acts as a fuel cell and is comprised of a centrally placed membrane electrode assembly upon each side of which is positioned a current collector which has gas inlets that allow gas to flow to the membrane electrode assembly. Plates are positioned on each of the exterior surfaces of the current collectors such that when assembled, one side of the CO sensor forms an anode and the other side forms a cathode. At a constant voltage, a sample gas passes through the sensor such that low levels of Platinum on the sensor facilitate the detection of carbon monoxide. A reader attached to the sensor interprets the concentration of carbon monoxide and air is passed through the sensor for recalibration as needed.

40 Claims, 5 Drawing Sheets

DETECTION OF CARBON MONOXIDE IN HYDROGEN-BASED GAS STREAMS

CROSS REFERENCE TO RELATED APPLICATIONS

This application claims priority to and incorporates by reference U.S. Provisional Application No. 60/361,634 filed Feb. 28, 2002, entitled "Detection Of Carbon Monoxide In Hydrogen-Based Gas Streams."

BACKGROUND OF THE INVENTION (1) Technical Field

The present invention relates to techniques detecting concentrations of carbon monoxide. More specifically, the present invention relates to detecting and removing carbon monoxide in a hydrogen-based gas stream.

(2) Discussion

There are many examples where detection and quantification of carbon monoxide (CO) in hydrogen streams is necessary. Perhaps the most urgent application, however, is for the emerging fuel cell vehicle. The current strategy by automobile manufacturers developing fuel cell cars is to produce hydrogen gas onboard the vehicle via the reformation of either methanol or gasoline. In both cases, the reformation process produces a fuel cell feed stream containing hydrogen, but also carbon dioxide ($CO_2$), water and small amounts of CO. The CO constituent has the effect of positioning the fuel cell at levels as low as 25 ppm. Therefore a method that allows for the monitoring and detection of CO at levels of greater than or equal to 25 ppm is desired.

Presently, the only reliable technique for sensing CO in hydrogen-based gas streams is by infrared absorption spectroscopy. However, to resolve species at very low levels, the intrinsic drift of the instrument and the interference from other species present in large concentrations, such as $CO_2$ (at 18% by volume) and water (at 99% relative humidity) must be eliminated or compensated for during the measurement. While the infrared approach is viable, it does not represent a low-cost solution compatible with today's vehicle sensors or other commercial applications where such sensors would be useful.

Other sensors based on electrochemical approaches, while lower in cost, demonstrate similar interference problems with both hydrogen and water in the process gas stream. Since the hydrogen content in the target process stream is near 50% by value, with a relative humidity of 90-99%, detection of low levels of CO is not possible. At present, most fuel cells have attempted to address the problems associated with CO presence in the cell by designing the anode of the cell to avoid the effects of CO. Strategies include using high concentration of Platinum ($\geq 1.0$ mg/cm2) or CO insensitive alloys of Platinum (e.g., Pt/Ru) in a membrane electron assembly forming part of the fuel cell.

Many other sensors that measure CO in air have been developed based on biomimetic, electrochemical, and resistive-based elements. They represent a low-cost approach for home or laboratory monitoring where the hydrogen concentration in the target gas is minimal. Each of these approaches, however, has a strong interference from hydrogen and is incapable of making accurate CO determinations when this interfering species is present in abundance.

Accordingly, there exists a need in the art for a reliable, reusable and low-cost system for detecting CO in desired gas streams. There is also a need for a system that can meet the aforementioned requirements while having the relatively low response time and freedom from interference when performing CO measurements.

SUMMARY OF THE INVENTION

The present invention provides a carbon monoxide sensor, a method for making such, and a system for detecting carbon monoxide in a hydrogen-based gas stream. In a first aspect, the present invention is a carbon monoxide sensor comprising: a membrane electrode assembly for facilitating proton exchange having a proton-exchange membrane with and anode and a cathode side and an electrically conductive coating comprising a concentration of platinum for covering at least a portion of each of the anode side and the cathode side of the proton-exchange membrane, an anode for facilitating dissociation of hydrogen having a first current collector and a first plate which is electrically connected to the exterior surface of the first current collector; and a cathode for receiving a current of electricity for delivery to the membrane electrode comprising a second current collector and a second plate which is connected to the exterior surface of the second current collector, wherein the membrane electrode assembly, the anode and the cathode are electrically connected for transmitting a current and facilitating a proton-exchange reaction.

In one aspect of the invention, the electrically conductive coating is carbon, while in another aspect, the electrically conductive coating is a carbon black paste having a concentration of platinum.

In a further aspect of the present invention, the first and the second current collector each comprise at least one channel which allows the sample gas stream to flow to the electrically conductive coating on the membrane electrode assembly while in another aspect, the first and the second current collector each comprise at least one inlet for allowing the sample gas stream to flow to the electrically conductive coating on the membrane electrode assembly.

Another aspect of the present invention provides for a proton-exchange membrane which is a Nafion-based proton-exchange membrane. In additional aspects, the first plate and the second plate are comprised of gold-anodized copper, the first current collector and the second current collector are comprised of graphite, the anode and the cathode comprise electrical connections for connecting to an electrical supply, and the anode is attached to a reader for activating a gas selection valve and for measuring current through the circuit.

In a further aspect, the sensor of the present invention is approximately 4.25 inches high, 3.75 inches wide, and 1.625 inches thick.

In an additional aspect, the reader is programmable for converting changes in a measured current caused by a concentration of carbon monoxide in the sample gas stream.

In yet another aspect of the present invention, the sample gas source delivers gas with an approximately 2.0 second exposure time and the air source delivers air with an approximately 0.5 second air exposure time thereby allowing a detection of approximately $\leq 50$ ppm carbon monoxide in the sample gas stream, while in another aspect sensitivity to $\geq 25$ ppm carbon monoxide is feasible using a greater than 2.0 second exposure time to the sample gas and an approximately 0.5 second air recovery cycle. In one aspect, this sample gas stream is a hydrogen-based gas stream.

In a further aspect, the cathode is attached to a resistor for maintaining the potential of the cell at a constant value during closed-circuit operation, and in yet another aspect, the cathode is attached to a constant voltage sink for maintaining the potential of the cell at a constant value during closed-circuit operation.

The present invention, in a further aspect, comprises a resistance patch heater electrically connected to the membrane electrode assembly, the anode and the cathode, wherein the resistance patch heater is attached to a temperature controller for maintaining the sensor's temperature.

In a further aspect, the carbon monoxide sensor of the present invention operates at a temperature in a range from approximately 63°-82° Celsius, where this range corresponds to a temperature within 1.0° to 2.0° Celsius of the sample gas temperature.

Additional aspects of the present invention provide for an anode that is attached to a selection valve for delivering ambient air and the sample gas to the carbon monoxide sensor, an approximately 1.0 mg/cm$^2$ concentration of platinum in the anode, a concentration of platinum ranging from approximately 0.001 mg/cm$^2$ to 1.0 mg/cm$^2$, and an aspect in which the cell potential is maintained at approximately 0.3 Volts.

The present invention also provides for a system for measuring carbon monoxide in a gas stream comprising: a sensor for detecting carbon monoxide having an anode, membrane electrode assembly, and a cathode; a reader for calculating a change in current to carbon monoxide concentration; a sample gas source for supplying a sample gas stream to the sensor; an air source for supplying air to the sensor; a selection valve for controlling the supply of the sample gas stream and the air to the anode; a temperature controller for controlling the temperature of the sensor, and a voltage controller for maintaining a constant closed-cell voltage potential.

Another aspect provides for a temperature controller which comprises a resistive heating unit and a thermocouple arrangement for controlling a resistance patch heater coupled to the sensor to maintain a desired temperature.

In further aspects, the voltage controller is a constant voltage sink, and the voltage controller is a resistor.

Additional aspects provide for the use of ambient air, an anode comprising a carbon black coating, an anode and cathode which comprise a current collector having at least one channel for allowing gas to flow to the membrane electrode assembly, and an anode and a cathode which comprise a current collector having at least one inlet for allowing gas to flow to the electrically conductive coating on the membrane electrode assembly.

The system of the present invention may also include a Nafion-based proton exchange membrane and an anode and a cathode comprising a first plate and a second plate respectively. In yet further aspects, the first plate and the second plate are comprised of gold-anodized copper and the anode and the cathode comprise a first current collector and a second current collector respectively, wherein the first current collector and the second current collector are comprised of graphite.

In another aspect, the anode is attached to the reader for activating a gas selection valve, measuring current through the circuit, and calculating the concentration of carbon monoxide in the sample gas stream, and in a further aspect, the reader is programmable for converting changes in a measured current caused by carbon monoxide in the sample gas stream.

In still another aspect, the sample gas source delivers a sample gas with an approximately 2.0 second exposure time and the air source delivers air for an approximately 0.5 second air recovery cycle, thereby allowing a detection of approximately 50 ppm carbon monoxide in the sample gas stream.

In a further aspect, the sample gas source delivers gas for an exposure time ranging between 2.0 to 30 seconds and the air source delivers air for an approximately 0.5 second air recovery cycle, thereby allowing a detection of $\geq$25 ppm carbon monoxide in the sample gas stream.

In another aspect, the cathode is attached to a resistor for maintaining the potential of the cell at a constant value during closed-circuit operation, and in an additional aspect, the invention includes a constant voltage sink for maintaining a constant cell potential during closed-circuit operation.

The system may also include a temperature controller is attached to a resistance patch heater on the sensor for controlling temperature, and in one aspect, operates at a temperature in a range from approximately 63°-82° Celsius, wherein the range corresponds to a temperature within 1.0° to 2.0° Celsius of the sample gas temperature.

In still further aspects, the anode is attached to a selection valve for delivering ambient air and the sample gas to the sensor, the sensor comprises a concentration of platinum of approximately $\leq$1.0 mg/cm$^2$ near the cathode and a concentration of platinum in a range of 0.0001 mg/cm$^2$ to 1.0 mg/cm$^2$ near the anode, and the cell potential is maintained at approximately 0.3 Volts.

The present invention also provides for a method of measuring carbon monoxide in a gas stream comprising steps of: providing a current at an original rate to a sensor; cycling a selection valve for sequentially exposing the sensor to a sample gas stream which includes delivering the sample gas stream to the sensor from a sample gas source; switching the selection valve to a position for delivering air after exposing the sensor to the sample gas stream; delivering air to the sensor from an air source; and switching the selection valve to a position for delivering the sample gas after exposing the sensor to the air; measuring a fluctuation in the current being delivered to the sensor; calculating a carbon monoxide concentration in the sample gas stream by translating the fluctuation in the current to a concentration of carbon monoxide; removing carbon monoxide from the sensor as air is exposed to the sensor; and restoring the current to the original rate.

In an additional aspect, the method measuring carbon monoxide is in a hydrogen-based gas stream, and in a further aspect, the delivering of the sample gas stream is to an anode portion of the sensor, which in another aspect, platinum is present in the anode at a concentration of 0.001 mg/cm$^2$ to 1.0 mg/cm$^2$.

Further aspects of the method of the present invention include exposing the sensor to air for approximately $\leq$1 second, removing carbon monoxide by oxidation from the sample gas stream during the step of exposing the sensor to the air, removing carbon monoxide from the sample gas stream in $\leq$1 second, calibrating a reader before measuring a change in the current, and controlling the steps of delivering a stream of gas and delivering air with the selection valve.

In another aspect, the steps of measuring a fluctuation in current and calculating a carbon monoxide concentration are facilitated by the reader which is electrically coupled to the sensor.

In still a further aspect, the invention includes a step of measuring a decrease in the current when carbon monoxide is present in the gas stream.

The invention may also include a step of exposing the sensor to the sample gas stream for approximately 2 to 30 seconds.

Additionally, in a further aspect, the present invention provides for repeating the steps of providing a current, cycling a selection valve, measuring a fluctuation in the current, calculating a carbon monoxide concentration in the sample gas stream, removing carbon monoxide from the sensor as air is exposed to the sensor, and restoring the current for obtaining a subsequent measurement of carbon monoxide in the sensor.

In still further aspects of the method of measuring carbon monoxide in a gas-stream system, the invention provides for maintaining the current at a constant voltage, which in one aspect is approximately 0.3 Volts, and controlling temperature of the sensor through a resistance patch heater electrically coupled to the sensor and a temperature controller.

The present invention also provides for a method of forming a carbon monoxide sensor comprising steps of: providing a membrane electrode assembly to facilitate proton exchange which includes: providing a proton-exchange membrane; and applying an electrically conductive coating to at least of portion of each of opposite sides of the proton-exchange membrane, wherein the electrically conductive coating comprises a concentration of platinum; forming an anode by attaching a first plate to an exterior surface of a first current collector; forming a cathode by attaching a second plate to an exterior surface of a second current collector; and coupling the cathode to one side of the membrane electrode assembly and the anode to the opposite side of the membrane electrode assembly for electrical communication with the membrane electrode assembly, thereby forming a sensor for detecting carbon monoxide concentrations in a gas stream.

In additional aspects, the method of forming a carbon monoxide sensor further comprises steps of forming a channel on at least one of the first and the second current collector, wherein the channel facilitates a flow of the gas stream to the electrically conductive coating on the membrane electrode assembly and forming an inlet on at least one of the first and the second current collector, wherein the channel facilitates a flow of the gas stream to the electrically conductive coating on the membrane electrode assembly.

In still a further aspect, the invention includes electrically coupling a resistance patch heater to the sensor for maintaining the sensor at a desired temperature.

BRIEF DESCRIPTION OF THE DRAWINGS

The objects, features and advantages of the present invention will be apparent from the following detailed descriptions of the preferred aspect of the invention in conjunction with reference to the following drawings.

DETAILED DESCRIPTION OF PREFERRED ASPECTS

The present invention relates to a sensor and related techniques for measuring carbon monoxide. More specifically, the present invention relates to measuring low amounts of carbon monoxide (CO) in gas streams such as hydrogen-based gas streams present in fuel cell vehicles. The following description, taken in conjunction with the referenced drawings, is presented to enable one of ordinary skill in the art to make and use the invention and to incorporate it in the context of particular applications. Various modifications, as well as a variety of uses in different applications, will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein. Furthermore it should be noted that unless explicitly stated otherwise, the figures included herein are illustrated diagrammatically and without any specific scale, as they are provided as qualitative illustrations of the concept of the present invention.

In order to provide a working frame of reference, an introduction of various physical aspects of the present invention and the nature of their impact is provided first followed by a discussion to give an understanding of the specific details.

(1) Introduction

The CO sensor described herein is based upon many of the same principles as the modern day fuel cell. To understand how the sensor operates, one must become familiar with the factors influencing the performance of a typical proton exchange membrane (PEM)-based fuel cell. In a typical PEM of a fuel cell, hydrogen, or a process gas containing hydrogen, is supplied to the anode of the PEM, with air supplied to the cathode. At the anode, hydrogen is catalytically dissociated into protons and electrons. The protons then diffuse through the PEM to the cathode, while the electrons flow through to an external circuit. When the protons reach the cathode, the protons recombine with electrons from the circuit and with oxygen from the air to produce water. This process represents the normal operation of a fuel cell in absence of CO.

To understand the effects of carbon monoxide, and hence the basis for the present invention, one must look more closely at the dissociation process for hydrogen at the anode side of the fuel cell. Carbon is present on the polymer-based PEM. This carbon not only provides an electrical contact to the PEM, but also contains finely divided particles of platinum (Pt) that act as a catalyst for the dissociation of hydrogen. In the event that CO comes into contact with the Pt particles, a bond is formed and the molecule tends to remain on the particle surface. If the coverage of the CO on the Pt particle surface becomes significant (i.e., a "poisoning" effect), the dissociation of hydrogen is inhibited by the presence of CO, thereby limiting the performance of the fuel cell. Poisoning from CO manifests as either a decrease in the operating voltage of the cell or as a decrease in the cell output current.

The performance decline in the fuel cell as a result of CO exposure is manifested by either a decrease in the observed potential, or in the current during closed-circuit operation. An open-cell potential is the difference between the measured potentials at the cathode and the anode, and is determined by the standard free energy change for the chemical reaction between hydrogen and oxygen. Notably, the open-cell potential is not affected by the presence of CO. Once the cell is closed, however, the measured potential becomes a function of several parameters, including a CO-related polarization at the anode. It may be inferred that both the current through the cell and the polarization at the electrodes will contribute to the measured cell potential. Alternatively, if the closed-cell potential is fixed, then a change in the anode polarization must be accompanied by an equal and opposite magnitude change in the current (assuming cathode polarization is zero and the resistance of the circuit is constant). Hence, by utilizing a hardware design that forces the cell potential to remain constant, one can measure the CO-induced polarization of the anode (i.e., poisoning) through measured changes in the cell current. Furthermore, through proper calibration, a relationship between the decrease in observed current and the concentration of CO at the anode (or the process stream) may be derived.

While it has been expressed in patent literature (U.S. Pat. No. 5,712,052) that a CO sensor based on a fuel cell might be part of an electrical generator system, no details of how such a sensor would operate, or description of the sensor in general is given. It is also true that many groups have studied and modeled the poisoning phenomenon of the fuel cell anode by CO. However, it has not been suggested how to utilize the poisoning phenomenon as the basis of a sensor for CO, or how to conveniently recover the sensor for continued use while maintaining a constant voltage. The CO sensor of the present invention is based on the same poisoning effects experienced by the fuel cell stack itself. In fact, the sensor represents a miniaturized version of a single fuel cell element, modified to be orders of magnitude more sensitive to CO poisoning. As such, the sensor is inherently able to operate in a fuel cell environment, is vehicle compatible, and has a lifetime equivalent to the primary fuel cell stack. The sensor also could be integrated with the fuel cell stack of the vehicle, thereby eliminating the need for a separate, stand-alone device. In this configuration, the sensor could have the unusual role of actually providing power to a vehicle while measuring the CO content in the feed stream.

The present invention comprises a method of detecting low levels (i.e., $\geq 25$ ppm) of carbon monoxide (CO) in a gas stream containing mostly hydrogen, little or no oxygen, and having a high moisture (water) content at temperatures in the range of approximately 50-85° Celsius. The described sensor is capable of sampling, measuring, and outputting the CO content of a gas stream in approximately 2.5 seconds during normal operation (for example, after a brief warm-up period) with no interference from carbon dioxide ($CO_2$), nitrogen, or water vapor. At present, no other sensor appears to have the sensitivity, response time and freedom from interference when performing CO measurements at a constant voltage in similar gas streams. Additionally, to accomplish such advantages, the present invention includes the following important features: 1) an operation of the fuel cell element at a fixed potential (approximately 0.3 V) where the current density and susceptibility to CO poisoning are near or at a maximum; 2) a modification of the anode chemistry in the sensor such that its sensitivity and response to CO poisoning is at a maximum; and 3) a method for returning the sensor current to a reproducible baseline using air after performing a CO measurement on a sample gas.

(2) Physical Aspects

Figure 1:
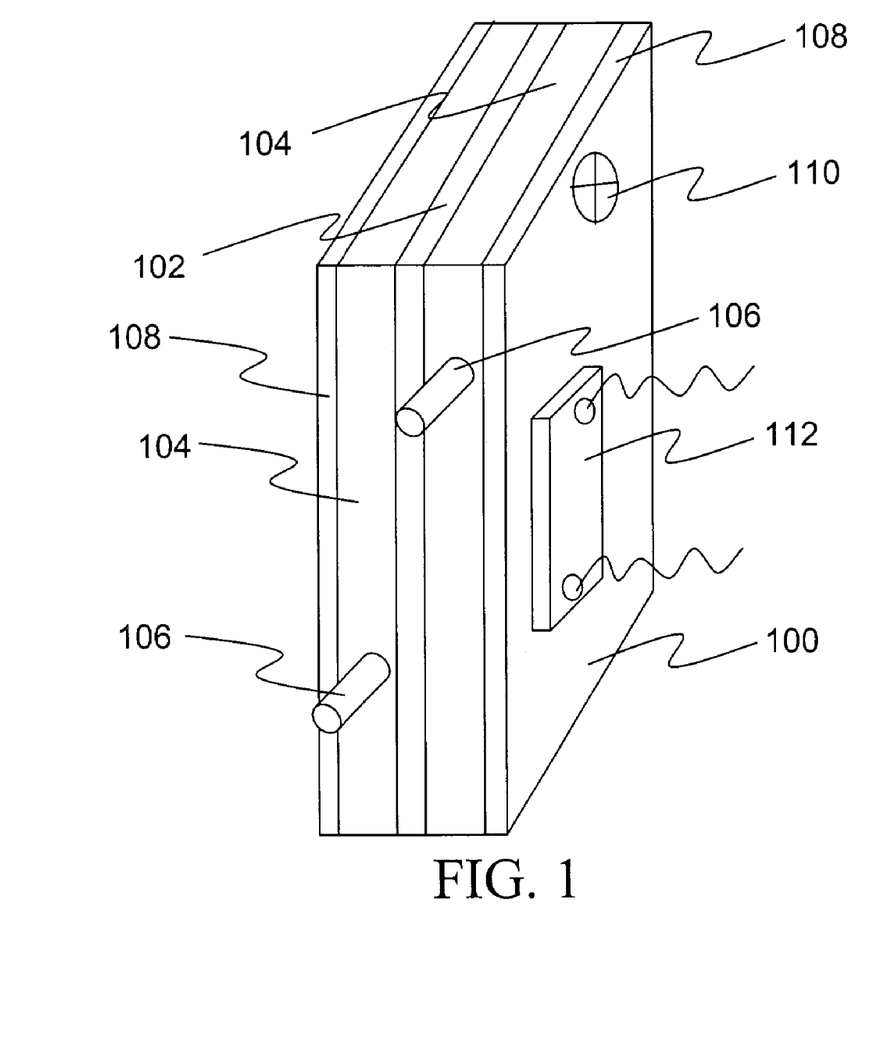
FIG. 1 is a front perspective view of one aspect of the carbon monoxide sensor of the present invention.

FIG. 1 presents a front perspective view of the carbon monoxide (CO) sensor 100 of the present invention. The CO sensor 100, which acts as a fuel cell, is comprised of a centrally placed membrane electrode assembly (MEA) 102 and a current collector 104 positioned on each of opposite sides of the MEA 102. In one aspect of the invention, the current collectors 104 are comprised of graphite in the form of a graphite block. The current collectors 104 may have gas inlets 106 that allow for the flow of gas to the MEA. On each of the exterior surfaces of the current collectors 104 is a plate 108. When assembled, one side of the CO sensor 100 forms and anode 304 (see FIG. 3) while the opposite side forms a cathode 110. The temperature at which the sensor operates is maintained by a resistance patch heater 112 which is attached to one of the plates 108 and further connected to a temperature controller 306 (see FIG. 3). A non-limiting example of the resulting CO sensor 100, as depicted, is approximately 4.25 inches high, 3.75 inches wide, and 1.625 inches thick.

Figure 2:
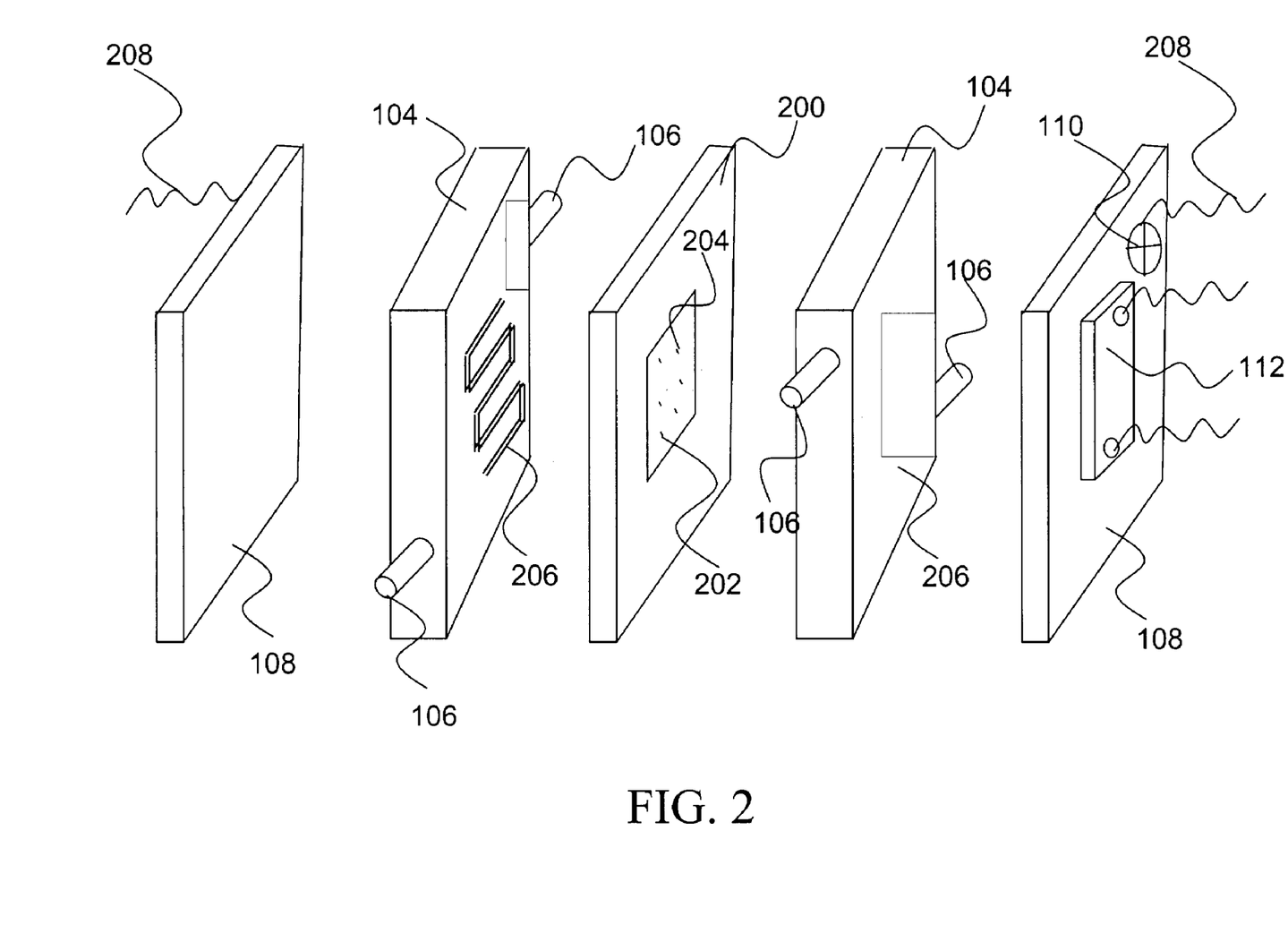
FIG. 2 is an exploded view of the sensor of the present invention, showing the membrane electrode assembly, the plates, and the current collectors that form the sensor.

FIG. 2 is an exploded view of the present invention which more closely depicts the individual components that comprise the CO sensor 100. The centrally positioned MEA 102 is comprised of a proton exchange membrane 200, which may be a Nafion-based proton exchange membrane. The proton exchange membrane 200 is coated on each side with an electrically conductive coating 202. The electrically conductive coating 202 is a carbon black paste containing an approximately 0.001 to 1.0 $mg/cm^2$ concentration of finely-divided Platinum particles 204. A decrease in the Platinum concentration enhances the effects of the CO which is observed by a decrease in current output by the CO sensor 100. Thus, a 0.01 or 0.005 Platinum/$cm^2$ concentration is desirable to provide for the most rapid CO sensor 100 response to CO. The current collectors 104 are positioned on each side of the proton exchange membrane 200 and thus are in contact with the electrically conductive coating 202. As noted in reference to FIG. 1, these current collectors 104 are comprised of graphite in the form of a graphite block and have gas inlets 106 which facilitate the flow of gas. In addition to the gas inlets 106, the current collectors 104 also may have grooved channels 206 on their interior surface that allow for gas flow to the carbon black paste/Platinum-coated region of the MEA 102. On the exterior surface of each of the current collectors 104 is a plate 108, which may be comprised of gold-anodized copper. The plates 108 provide the housing and location for an electrical connection 208 to the CO sensor 100. Together, the proton exchange membrane 200, the current collectors 104 and the plates 108 form the sensor 100 having an anode 304 side and a cathode 110 side.

Figure 3:
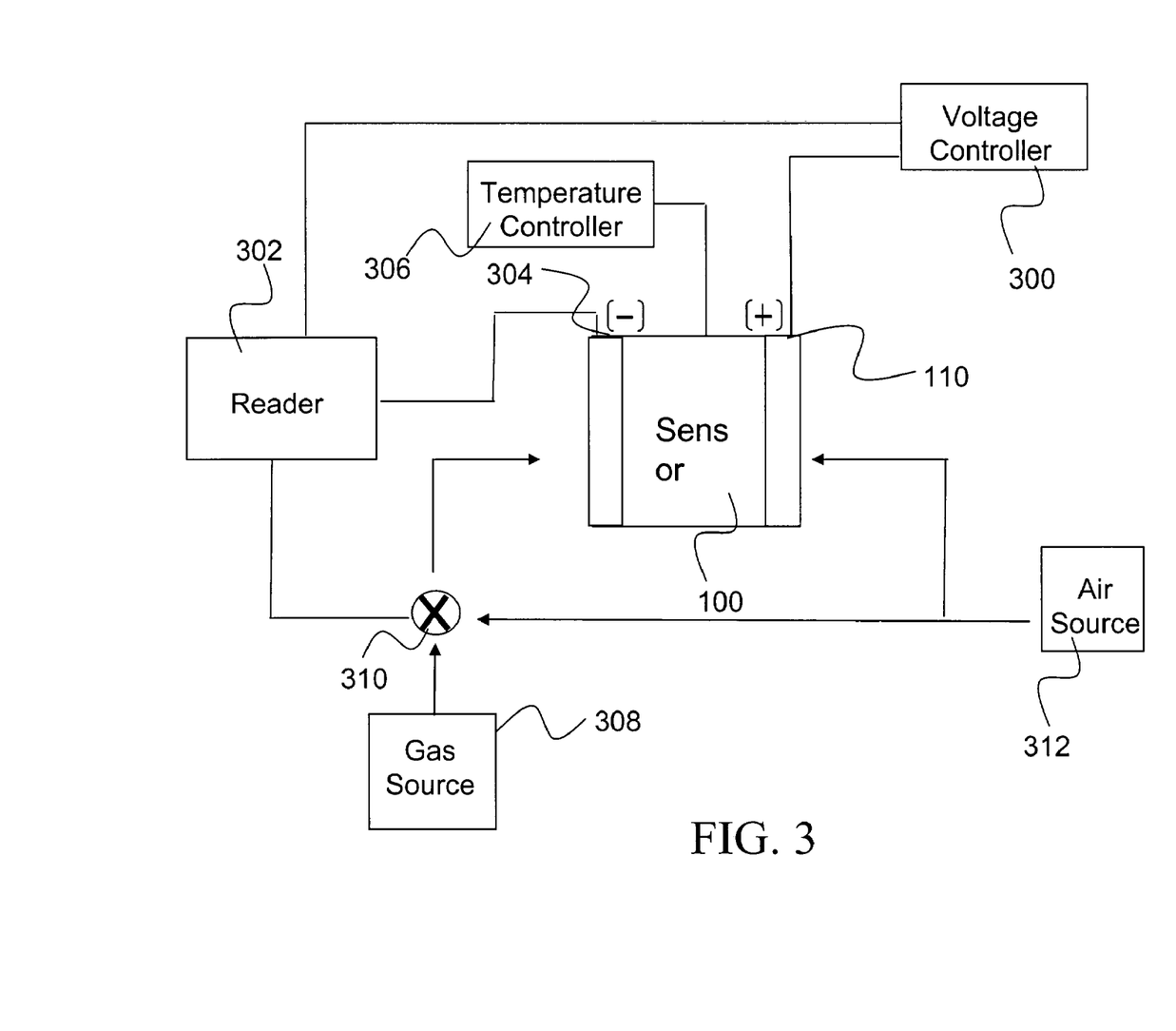
FIG. 3 is a schematic diagram of a system of detecting carbon monoxide, incorporating the sensor of the present invention.

FIG. 3 depicts the CO sensor 100 integrated into a hardware scheme which thereby allows for measurement of CO in a sample gas stream. The CO sensor 100 is attached to a voltage controller 300 near the cathode 110 of the CO sensor 100 and a reader 302 at the anode 304. The voltage controller 300 allows the potential of the CO sensor 100, acting as a fuel cell during closed circuit operation, to be maintained at a constant value. The voltage controller 300 may be a resistor or a circuit that is capable of sustaining a constant voltage in the event of a sinking current. Additionally, the reader 302, which is an ammeter having programmable circuitry and a display, is provided in series with the constant voltage circuit. The reader 302, which may be a handheld reader, acts to periodically activate the flow of gas to the CO sensor 100 and to measure current through the circuit. The reader 302 is programmed to convert changes in measured current caused by CO "poisoning" into concentration of the CO species in a gas stream that is delivered to the CO sensor 100. The temperature of the CO sensor 100 is controlled using a temperature controller 304 which is connected to the CO sensor 100 through the resistance patch heater 112. The temperature controller 306 is of a type commonly used in the art and may include a resistive heating unit and thermocouple arrangement. The temperature controller 306 allows the temperature of the CO sensor to be maintained within approximately 1-2 degrees Celsius of the temperature of a sample gas being supplied to the CO sensor 100, where the temperature of the sample gas is approximately 65-80 degrees Celsius. During operation of the CO sensor 100, a sample gas stream is delivered from a sample gas source 308 to the CO sensor 100. The sample gas stream, which contains hydrogen (and potentially other gases including CO), is passed through a selection valve 310 to the gas inlet 106 and channels 206 that feed the anode 304 side of the CO sensor 100. An air source 312 delivers air to both a selection valve 310 and the cathode 110 side of the CO sensor 100 in a similar manner. Ideally, the flow rate, temperature, and humidity of the ambient air fed to the cathode 110 are such that the proton exchange membrane 200 does not become unnecessarily dry. In practice, this can be achieved since water is produced in the cathode 110 by virtue of the overall CO sensor 100 fuel cell reaction.

In the present invention, quantification of the CO concentration is achieved by examining the decrease in current from a fixed baseline for a specific time period. The present invention obtains the same baseline current at the beginning of each measurement by refreshing the sensor to its original, "unpoisoned" state, before a measurement is subsequently performed on the sample gas. The situation is somewhat complicated by the fact that the amount of CO in the sample gas stream is dynamic, thereby making the amount of poisoning during a measurement cycle variable. The degrees of CO poisoning is also dependent on the Platinum content 202 in the anode 304. Therefore, CO sensors with anodes 304 containing low Platinum concentrations 202, such as that provided in the present invention, allow for a trade-off between sensitivity and ability to recover from CO poisoning.

Thus, the measurement of the CO content in the gas stream is made possible by periodically cycling the selection valve 310 in between the sample gas source 308 and the air source 312. The reader 302 acts to periodically activate a gas selection valve 310, and to measure current through the circuit. In each cycle, the anode 304 side of the CO sensor 100 is sequentially exposed to the sample gas and then the air. During exposure to the sample gas, if CO is present in the sample gas stream, a measurable decrease in the current results as a consequence of the poisoning phenomenon previously described. The time period that the anode 304 is exposed to the sample gas may vary between approximately 2.0 to 30 seconds, depending on the desired sensitivity. Notably, sensitivity to CO is enhanced with longer exposure times. For example, a 2.0 second exposure to the sample gas stream allows for a measurement of $\geq 50$ ppm CO when using a methanol reformate (approximately 50% $H_2$, 16% $CO_2$, 17% $H_2O$, and 27% $N_2$) sample gas stream. Subsequent to the second gas exposure, the reader 302 translates the measured current decrease into a CO concentration. This measurement and translation is made possible through a prior calibration of the reader 302. During the air exposure cycle, CO is oxidatively removed from the platinum 204 in the anode 312, and the baseline current is temporarily restored to its original value. The air cycle is approximately $\leq 1.0$ second thereby allowing for rapid removal of CO.

The rapid response time of the CO sensor 100 to concentrations of CO $\geq 50$ ppm is able to be achieved because of the sensor's 100 modification of the anode 304 chemistry, and by operating the CO sensor 100 in a manner where it is most sensitive to the poisoning effects from the CO. For example, the anode 304 chemistry uses ultra-low Platinum concentrations ($\leq 1.0$ mg/cm$^2$) in the carbon black coating 202 which enhances CO poisoning. The CO sensor 100 also is more sensitive to CO poisoning when operated at high current densities. Likewise, the fuel cell is less likely to meet the demands for high current when any fraction of the Platinum is unavailable for catalysis of the reaction, thus, explaining why the Platinum concentration near the anode of the present invention is preferably low. Additionally, the use of an air flow across the anode 304 allows for the CO sensor's 100 rapid recovery of from CO poisoning.

Figure 4:
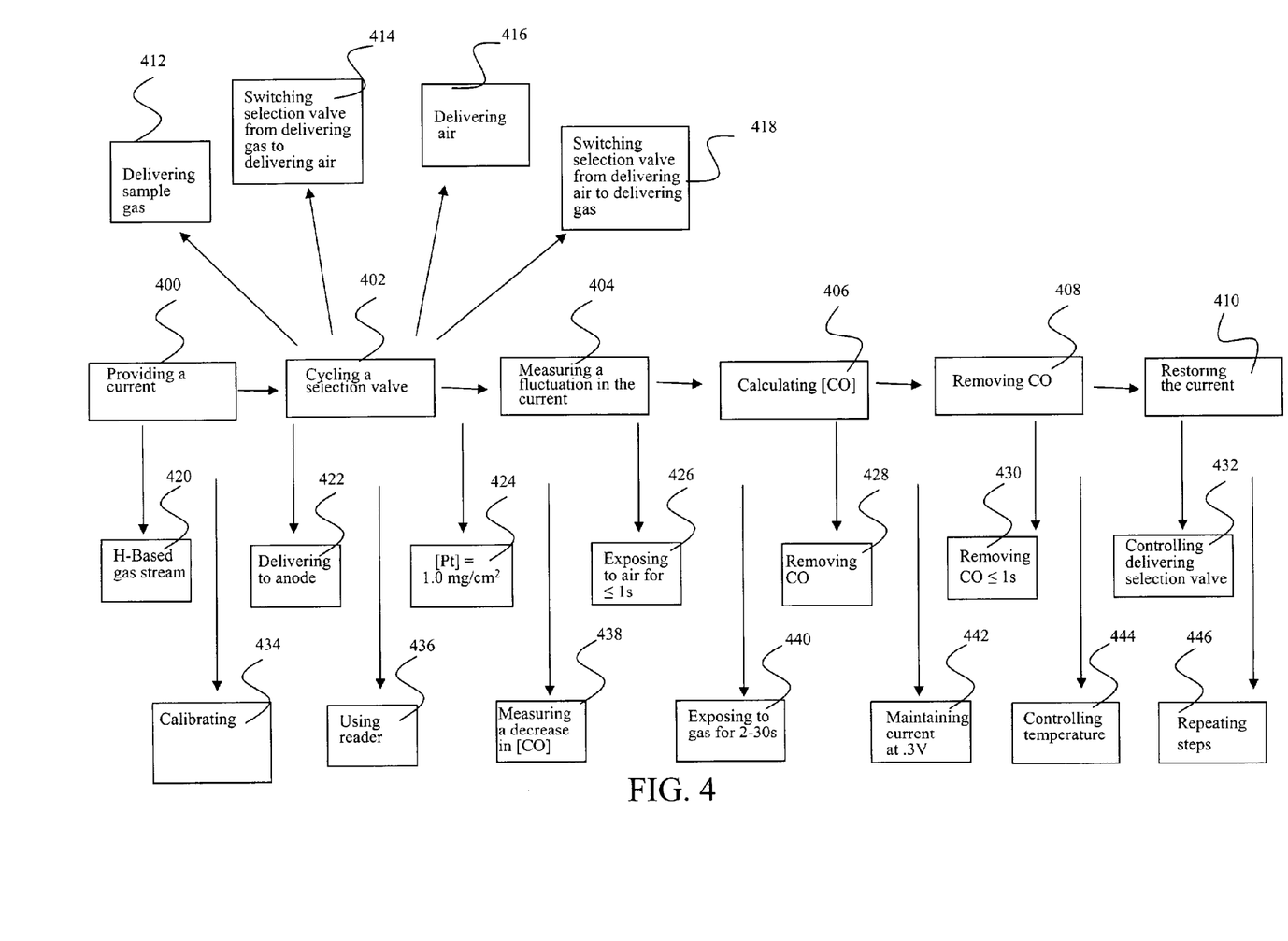
FIG. 4 is a process flow diagram of a method of producing a carbon monoxide sensor of the present invention.

FIG. 4 depicts a method of measuring CO in a gas stream utilizing the sensor 100 presented in FIGS. 1-3. The method includes the steps of: 1) providing a current 400 at an original rate to a sensor; 2) cycling a selection valve 402 for sequentially exposing the sensor to a sample gas stream and air; 3) measuring a fluctuation in the current 404 being delivered to the sensor; 4) calculating a CO concentration 406 in the sample gas stream by translating the fluctuation in the current to a concentration of CO; 5) removing CO 408 from the sensor as air is exposed to the sensor; and restoring the current 410 to the original rate. The step of cycling a selection valve includes the following substeps: 1) delivering the sample gas stream 412 to the sensor from a sample gas source; 2) switching 414 the selection valve from delivering sample gas to delivering air after exposing the sensor to the sample gas stream; delivering air 416 to the sensor from an air source; and closing the selection valve 418 after exposing the sensor to the air. In one aspect of the invention, the sample gas stream to which the method is applied is a hydrogen-based gas stream 420, and may also include delivering the sample gas source to the anode 422. Additionally, a $\leq 1.0$ mg/cm$^2$ concentration of platinum near the cathode and a 0.0001 to 1.0 mg/cm$^2$ concentration of platinum near the anode may be present in the sensor 424. The method may also include the steps of: exposing the sensor to air for approximately $\leq 1$ second 426; removing CO by oxidation from the anode during the step of exposing the sensor to the air 428; and removing CO from the anode in $\leq 1$ second 430. Furthermore, the steps of delivering a stream of gas and delivering air may be controlled by a selection valve 432. The method may also include calibrating a reader 434 before measuring a change in the current and measuring a fluctuation in current and calculating a CO concentration with the reader 436 which is electrically coupled to the sensor. In addition, the method may also involve a step of measuring a decrease in the current 438 when CO is present in the gas stream. In one aspect of the invention, the exposure of the sensor to the sample gas stream is for approximately 2 to 30 seconds 440 and in another aspect, the closed circuit potential of the sensor is maintained at a constant value of approximately 0.3 Volts 442 and in an even further aspect, the temperature of the sensor is controlled 444 through a resistance patch heater electrically coupled to the sensor and a temperature controller. The aforementioned steps may be repeated steps for a subsequent measurement of the CO in the sample gas stream 446.

Figure 5:
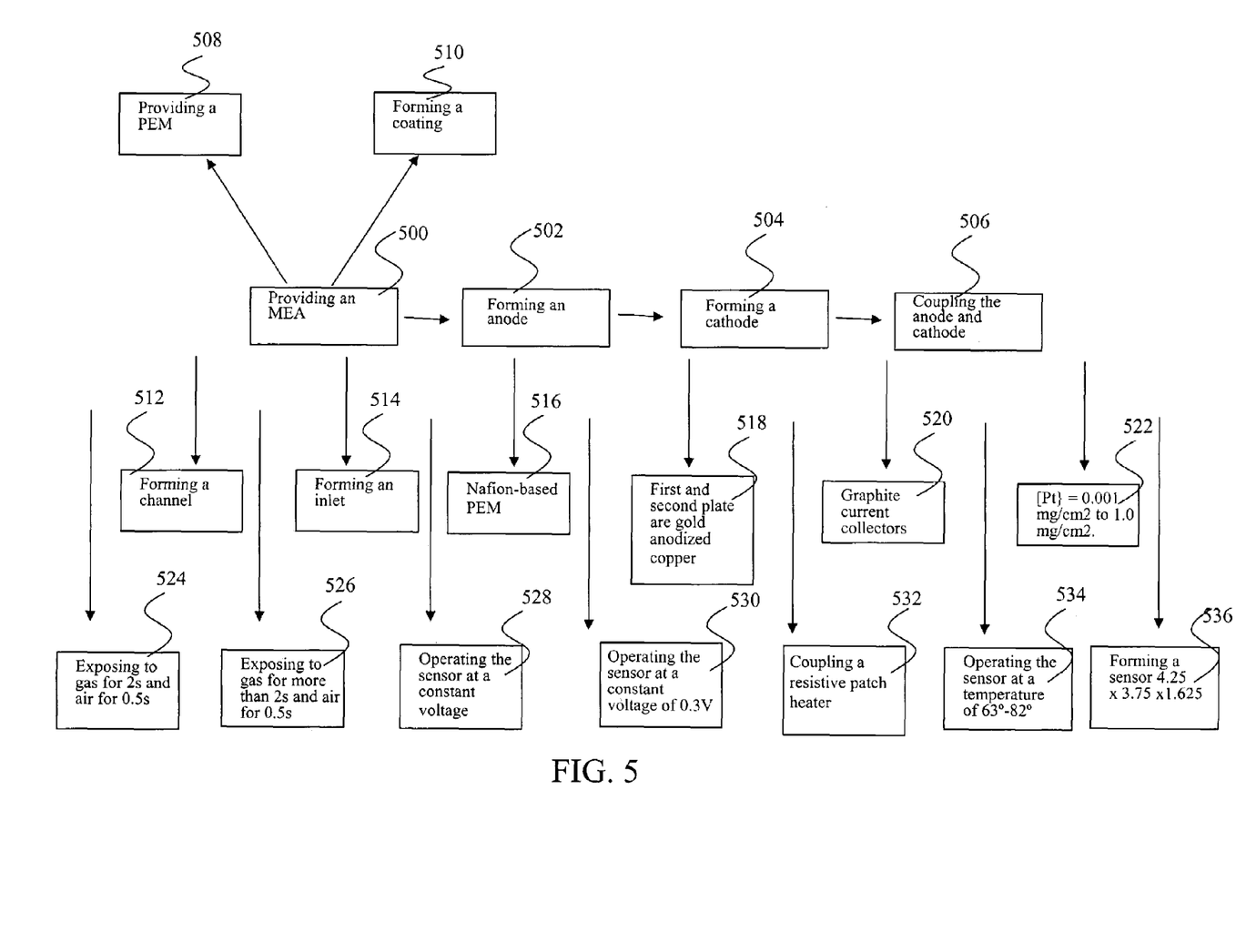
FIG. 5 is a process flow diagram of a method of detecting carbon monoxide in a gas stream.

FIG. 5 is a process flow diagram of a method of forming a CO sensor. The method include steps of: 1) providing a MEA 500 to facilitate proton exchange, 2) forming an anode 502 by attaching a first plate to an exterior surface of a first current collector; 3) forming a cathode 504 by attaching a second plate to an exterior surface of a second current collector; and 4) coupling the cathode 506 one side of the MEA and the anode to the opposite side of the membrane electrode assembly for electrical communication with the MEA, which thereby forms a sensor for detecting CO concentrations in a gas stream. The step of providing a MEA includes the substeps of providing a proton-exchange membrane 508 and applying an electrically conductive coating 510 which includes a concentration of Platinum on each side of the proton-exchange membrane. The method of forming a CO sensor may also include a step of forming a channel 512 and/or an inlet 514 on the first and the second current collector in order to facilitate a flow of the gas stream to the electrically conductive coating on the MEA. Additionally, the proton-exchange membrane may be a Nafion-based proton-exchange membrane 516, the first and second plate may be comprised of gold-anodized copper 518, and the first and second current collector may be comprised of graphite 520. A step of applying a concentration of Platinum to the electrically conductive coating in a range of approximately 0.001 mg/cm2 to 1.0 mg/cm$^2$ 522 may also be included in the method. Furthermore, the following steps may be included: exposing the anode to the sample gas stream for approximately 2.0 seconds and to air for approximately 0.5 second air for detecting approximately 50 ppm CO 524, exposing the anode to the sample gas stream for more than approximately 2.0 seconds and to air for approximately 0.5 second air for detecting $\leq$50 ppm CO 526, operating the sensor at a constant voltage 528, which may be approximately 0.3 Volts 530, electrically coupling a resistancepatch heater to the sensor for maintaining the sensor at a desired temperature 532, and operating the sensor at a temperature in a range from approximately 63°-82° Celsius 534, wherein the range corresponds to a temperature within 1.0° to 2.0° Celsius of the sample gas temperature. In one aspect of the invention, the method includes forming a sensor that is approximately 4.25 inches high, 3.75 inches wide, and 1.625 inches thick 536.

What is claimed is:

1. A carbon monoxide sensor comprising:
    a membrane electrode assembly for facilitating proton exchange comprising:
        a proton-exchange membrane for receiving electrical current, having an anode side and a cathode side, and an electrically conductive coating for covering at least a portion of each of the anode side and the cathode side of the proton-exchange membrane, wherein the electrically conductive coating comprises a concentration of platinum ranging from approximately 0.001 mg/cm$^2$ to 1.0 mg/cm$^2$;
    an anode connected with the anode side for facilitating dissociation of hydrogen comprising: a first current collector for collecting current, wherein the first current collector has at least one exterior surface, and comprises a first plate for providing an electrical connection, wherein the first plate is electrically connected to the exterior surface of the first current collector;
    a cathode connected with the cathode side for receiving a current of electricity for delivery to the membrane electrode comprising: a second current collector for collecting current, wherein the second current collector has at least one exterior surface, and comprises a second plate for providing an electrical connection, wherein the second plate is electrically connected to the exterior surface of the second current collector;
    a sample gas source for supplying a sample gas stream to the anode side of the sensor;
    an air source for periodically refreshing the carbon monoxide sensor to an unpoisoned state by supplying air to the anode side of the sensor;
    a voltage controller configured to maintain the closed-cell potential of the sensor at a constant potential;
    a reader in series with the voltage controller, the reader configured to measure the closed-cell current of the sensor; and
    an output configured to relate the inverse relationship between the closed-cell current of the sensor and the concentration of carbon monoxide (CO) present in the sample gas stream flowing through the anode side of the sensor;
    wherein the membrane electrode assembly, the anode, and the cathode are electrically connected for transmitting a current and facilitating a proton-exchange reaction when the sample gas stream and the air alternately flow through the anode side of the sensor, and wherein the transmitted current is used to quantify the carbon monoxide concentration in the sample gas stream.

2. A carbon monoxide sensor, as set forth in claim 1, wherein the electrically conductive coating comprises carbon.

3. A carbon monoxide sensor, as set forth in claim 2, wherein the electrically conductive coating comprises a carbon black paste having a concentration of platinum ranging from approximately 0.001 mg/cm' to 1.0 mg/cm'.

4. A carbon monoxide sensor, as set forth in claim 3, wherein the first and the second current collector each comprise at least one channel for allowing the sample gas stream to flow to the electrically conductive coating on the membrane electrode assembly.

5. A carbon monoxide sensor, as set forth in claim 4, wherein the first and the second current collector each comprise at least one inlet for allowing the sample gas stream to flow to the electrically conductive coating on the membrane electrode assembly.

6. A carbon monoxide sensor, as set forth in claim 5, wherein the proton-exchange membrane is a Nation-based proton-exchange membrane.

7. A carbon monoxide sensor, as set forth in claim 6, wherein the first plate and the second plate are comprised of gold-anodized copper.

8. A carbon monoxide sensor, as set forth in claim 7, wherein the each of the first current collector and the second current collector are comprised of graphite.

9. A carbon monoxide sensor, as set forth in claim 8, wherein the anode and the cathode further comprise electrical connections for connecting to an electrical supply.

10. A carbon monoxide sensor, as set forth in claim 9, further comprising a gas selection valve and a reader, wherein the anode is attached to the reader, and the reader activates the gas selection valve and measures current through the circuit.

11. A carbon monoxide sensor, as set forth in claim 10, wherein the reader is configured for converting changes in a measured current caused by a concentration of carbon monoxide in the sample gas stream into a quantification of carbon monoxide (CO) concentration, and wherein the reader sends the quantification of carbon monoxide (CO) concentration to the output of the carbon monoxide sensor.

12. A carbon monoxide sensor, as set forth in claim 11, wherein the sample gas source delivers gas with an approximately 2.0 second exposure time and the air source delivers air with an approximately 0.5 second air exposure time 13. A carbon monoxide sensor, as set forth in claim 12, wherein the sample gas stream is a hydrogen-based gas stream.

14. A carbon monoxide sensor, as set forth in claim 13, wherein the sample gas source delivers gas with an approximately greater than 2.0 second exposure time and the air source delivers air with an approximately 0.5 second air exposure time thereby allowing a detection sensitivity of approximately >25 ppm carbon monoxide in the sample gas stream.

15. A carbon monoxide sensor, as set forth in claim 14, wherein the cathode is attached to a resistor formed to maintaining a potential difference between the anode side and the cathode side at a constant value during closed-circuit operation.

16. A carbon monoxide sensor, as set forth in claim 15, the cathode is attached to a constant voltage sink for maintaining the potential difference between the anode side and the cathode side at a constant value during closed-circuit operation.

17. A carbon monoxide sensor, as set forth in claim 16, further comprising a resistance patch heater electrically connected to the membrane electrode assembly, the anode and the cathode, wherein the resistance patch heater is attached to a temperature controller for maintaining the sensor's temperature.

18. A carbon monoxide sensor, as set forth in claim 17, wherein the carbon monoxide sensor operates at a temperature in a range from approximately 63°-82° Celsius, wherein the range corresponds to a temperature within 1.0° to 2.0° Celsius of the sample gas temperature.

19. A carbon monoxide sensor, as set forth in claim 18, wherein the anode is attached to a selection valve for delivering ambient air and the sample gas to the carbon monoxide sensor.

20. A carbon monoxide sensor, as set forth in claim 19, wherein the concentration of platinum in the anode is approximately 1.0 mg/cm.

21. A carbon monoxide sensor, as set forth in claim 20, wherein the potential is maintained at approximately 0.3 Volts.

22. A carbon monoxide sensor, as set forth in claim 1, wherein the electrically conductive coating comprises a carbon black paste having a concentration of platinum ranging from approximately 0.001 mg/cm' to 1.0 mg/cm$^2$.

23. A carbon monoxide sensor, as set forth in claim 1, wherein the first and the second current collector each comprise at least one channel for allowing the sample gas stream to flow to the electrically conductive coating on the membrane electrode assembly.

24. A carbon monoxide sensor, as set forth in claim 1, wherein the first and the second current collector each comprise at least one inlet for allowing the sample gas stream to flow to the electrically conductive coating on the membrane electrode assembly.

25. A carbon monoxide sensor, as set forth in claim 1, wherein the proton-exchange membrane is a Nafion-based proton-exchange membrane.

26. A carbon monoxide sensor, as set forth in claim 1, wherein the first plate and the second plate are comprised of gold-anodized copper.

27. A carbon monoxide sensor, as set forth in claim 1, wherein the each of the first current collector and the second current collector are comprised of graphite.

28. A carbon monoxide sensor, as set forth in claim 1, wherein the anode and the cathode further comprise electrical connections for connecting to an electrical supply.

29. A carbon monoxide sensor, as set forth in claim 1, further comprising a gas selection valve and a reader, wherein the anode is attached to a the reader, and the reader activates the gas selection valve and measures current through the circuit.

30. A carbon monoxide sensor, as set forth in claim 1, wherein the anode is attached to a reader for activating a gas selection valve and measuring current through the circuit and the reader is configured for converting changes in a measured current caused by a concentration of carbon monoxide in the sample gas stream into a quantification of carbon monoxide (CO) concentration, and wherein the reader sends the quantification of carbon monoxide (CO) concentration to the output of the carbon monoxide sensor.

31. A carbon monoxide sensor, as set forth in claim 1, wherein the sample gas source delivers gas with an approximately 2.0 second exposure time and the air source delivers air with an approximately 0.5 second air exposure time thereby allowing a detection of approximately <50 ppm carbon monoxide in the sample gas stream.

32. A carbon monoxide sensor, as set forth in claim 1, wherein the sample gas stream is a hydrogen-based gas stream.

33. A carbon monoxide sensor, as set forth in claim 1, wherein the sample gas source delivers gas with an approximately greater than 2.0 second exposure time and the air source delivers air with an approximately 0.5 second air exposure time thereby allowing a detection sensitivity of approximately >25 ppm carbon monoxide in the sample gas stream.

34. A carbon monoxide sensor, as set forth in claim 1, wherein the cathode is attached to a resistor for maintaining a potential difference between the anode side and the cathode side at a constant value during closed-circuit operation.

35. A carbon monoxide sensor, as set forth in claim 1, the cathode is attached to a constant voltage sink for maintaining a potential difference between the anode side and the cathode side at a constant value during closed-circuit operation.

36. A carbon monoxide sensor, as set forth in claim 1, further comprising a resistance patch heater electrically connected to the membrane electrode assembly, the anode and the cathode, wherein the resistance patch heater is attached to a temperature controller for maintaining the sensor's temperature.

37. A carbon monoxide sensor, as set forth in claim 1, wherein the carbon monoxide sensor operates at a temperature in a range from approximately 63°-82° Celsius, wherein the range corresponds to a temperature within 1.0° to 2.0° Celsius of the sample gas temperature.

38. A carbon monoxide sensor, as set forth in claim 1, wherein the anode is attached to a selection valve for delivering ambient air and the sample gas to the carbon monoxide sensor.

39. A carbon monoxide sensor, as set forth in claim 1, wherein the concentration of platinum in the anode is approximately 1.0 mg/cm$^2$.

40. A carbon monoxide sensor, as set forth in claim 1, wherein a potential difference between the anode side and the cathode side is maintained at approximately 0.3 Volts.

* * * * *